(12) United States Patent
Jo et al.

(10) Patent No.: US 6,555,571 B2
(45) Date of Patent: Apr. 29, 2003

(54) 3-METHYL -CHROMANE OR THIOCHROMANE DERIVATIVES

(75) Inventors: JaeChon Jo, Seoul (KR); KooHyeon Ahn, Kyunggi-do (KR); JuSu Kim, Kyunggi-do (KR); PilSu Ho, Kyunggi-do (KR); Kazumi Morikawa, Shizuoka (JP); Yoshitake Kanbe, Shizuoka (JP); Masahiro Nishimoto, Shizuoka (JP); MyungHwa Kim, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/149,750

(22) PCT Filed: Dec. 13, 2000

(86) PCT No.: PCT/KR00/01446

§ 371 (c)(1),
(2), (4) Date: Jun. 13, 2002

(87) PCT Pub. No.: WO01/42237

PCT Pub. Date: Jun. 14, 2001

(65) Prior Publication Data

US 2003/0013756 A1 Jan. 16, 2003

(30) Foreign Application Priority Data

Dec. 13, 1999 (KR) .............................. 99-57065

(51) Int. Cl.$^7$ ........................ A61K 31/38; A61K 31/35; C07D 335/04; C07D 311/04

(52) U.S. Cl. ........................ 514/432; 514/456; 549/23; 549/406

(58) Field of Search .................. 549/23, 406; 514/432, 514/456

(56) References Cited

U.S. PATENT DOCUMENTS 6,156,788 A * 12/2000 Bernardon
6,218,427 B1 * 5/2001 Ishizuka et al.
6,316,494 B1 * 11/2001 Jacobsen et al.
6,369,225 B1 * 5/2002 Vasudevan et al.
6,417,223 B1 * 7/2002 Sanders et al.

* cited by examiner

*Primary Examiner*—Deborah C. Lambkin
(74) *Attorney, Agent, or Firm*—Browdy and Neimark

(57) ABSTRACT

The present invention relates to 3-methyl-chromane or thio-chromane derivatives, pharmaceutically acceptable salts, stereoisomers or hydrates thereof, and an anti-estrogenic pharmaceutical composition which comprises the above compound as an active component.

11 Claims, No Drawings

3-METHYL-CHROMANE OR THIOCHROMANE DERIVATIVES

This APPLN is a 371 of PCT/KR00/01446 Dec. 13, 2000

TECHNICAL FIELD

The present invention relates to 3-methyl-chromane or thiochromane derivatives having anti-estrogenic activity. More specifically, the present invention relates to 3-methyl-chromane or thiochromane derivatives represented by the following formula (1):

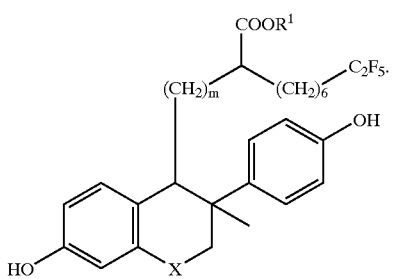

(1)

in which

X represents O or S, $R^1$ represents hydrogen or metal, and m represents an integer of 2 to 14, pharmaceutically acceptable salts, stereoisomers or hydrates thereof, and an anti-estrogenic pharmaceutical composition which comprises the compound of formula (1) as an active component.

BACKGROUND ART

In treating diseases that are dependent upon a certain sexual hormone such as estrogen, it is important to significantly reduce or inhibit the effect induced by the hormone. For this purpose, it is desirable to reduce the level of hormone capable of acting on the receptor site stimulated by sexual steroidal hormone. For instance, hysterectomy may be applied to limit the production of estrogen to the amount less than required to activate the receptor site. However, this method could not sufficiently inhibit the effect induced through the estrogen receptor. Practically, even when estrogen is completely absent, some of the receptors may be activated. Accordingly, it was considered that antagonists for estrogen can provide better therapeutic effect in comparison to the method for blocking only the production of sexual steroidal hormone (see, WO 96/26201). Thus, numerous anti-estrogenic compounds have been developed. For example, many patent publications including U.S. Pat. Nos. 4,760,061, 4,732,912, 4,904,661, 5,395,842 and WO 96/22092, etc. disclose various anti-estrogenic compounds. Sometimes, however, prior antagonists may act themselves as agonists, and therefore, activate rather than block the receptor. For example, Tamoxifen has been most widely used as an anti-estrogenic agent. However, it has a disadvantage that it exhibits estrogenic activity in some organs (see, M. Harper and A. Walpole, J. Reprod. Fertil., 1967, 13, 101).

As another non-steroidal anti-estrogenic compound, WO 93/10741 discloses a benzopyran derivative having aminoethoxyphenyl substituent (Endorecherche), the typical compound of which is EM-343 having the following structure:

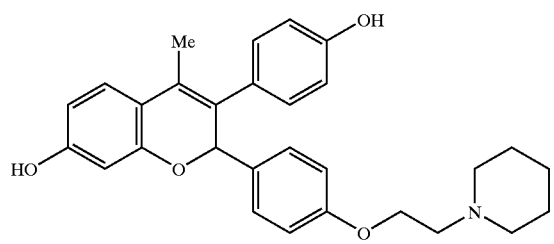

Said compound also has the agonistic effect. Therefore, it is required to develop an anti-estrogenic compound which has substantially or completely no agonistic effect and can effectively block the estrogenic receptor.

In addition, it has been known that 7α-substituted derivatives of estradiol, for example, 7α-$(CH_2)_{10}$CONBuMe derivatives, are steroidal anti-estrogenic agent without agonistic effect (see, EP Appl. 0138504, U.S. Pat. No. 4,659, 516). Further, estradiol derivative having 7α-$(CH_2)_9SOC_5H_6F_5$ substituent has also been disclosed (see, Wakeling et al., Cancer Res., 1991, 51, 3867).

Non-steroidal anti-estrogenic drug without agonistic effect has been first reported by Wakeling et al. in 1987 (see, A. Wakeling and J. Bowler, J. Endocrinol., 1987, 112, R7). Meanwhile, U.S. Pat. No. 4,904,661 (ICI, Great Britain) discloses a phenol derivative having anti-estrogenic activity. This phenol derivative mainly has a tetrahydronaphthalene structure and includes, typically, the following compounds:

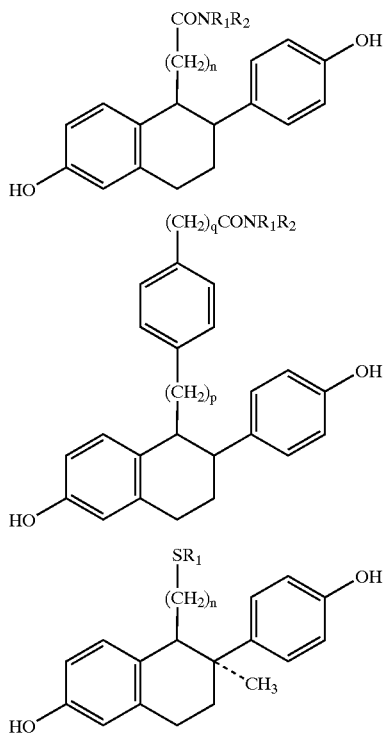

-continued

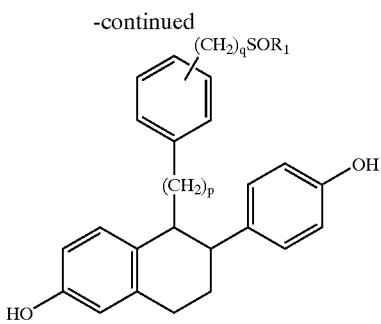

in which $R_1$, $R_2$, n, p and q are defined as described in the prior arts as mentioned above.

Some chromane and thiochromane derivatives have been reported as anti-estrogenic compounds having no agonistic effect (WO 98/25916). Although the existing anti-estrogenic compounds having no agonistic effect show a substantial therapeutic effect when administered via intravenous or subcutaneous injection, they show little therapeutic activity when administered orally, which is considered to be caused by several factors, one of which is the low bioavailability. Therefore, for convenience' sake in the case of administration, it is desired to develop anti-estrogenic compounds which show a sufficient effect when administered orally and at the same time have no agonistic effect.

DISCLOSURE OF THE INVENTION

Under these technical backgrounds, the present inventors have screened the anti-estrogenic activity of the new compounds having various structures. As a result, we have identified that 3-methyl-chromane or thiochromane derivatives represented by the following formula (1) can exhibit a good anti-estrogenic activity with no substantial agonistic effect even when orally administered, whereby we completed the present invention.

Therefore, the present invention relates to 3-methyl-chromane or thiochromane derivatives represented by the following formula (1):

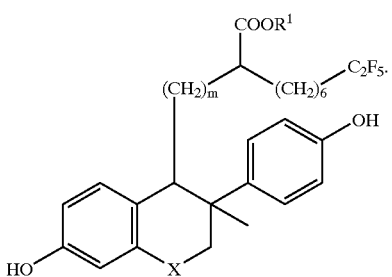

in which
X represents O or S,
$R^1$ represents hydrogen or metal, and
m represents an integer of 2 to 14, pharmaceutically acceptable salts, stereoisomers or hydrates thereof.

It is another object of the present invention to provide a medicine, more specifically an anti-estrogenic pharmaceutical composition which comprises the compound of formula (1) as an active component together with pharmaceutically acceptable carriers.

BEST MODE FOR CARRYING OUT THE INVENTION

In the compound of formula (1) according to the present invention, when $R^1$ is metal, $R^1$ may include alkali metals such as sodium, potassium, etc.; alkaline earth metals such as magnesium, calcium, etc.; rare earth metals such as cerium, samarium, etc.; and zinc, tin, etc. Among them, alkali metals and alkaline earth metals are more preferable, and alkali metals (particularly, sodium) are most preferable. When $R^1$ is a monovalent metal such as an alkali metal, the $R^1$ group combines with the residue of the compound of formula (1) in a ratio of 1:1. However, when $R^1$ is other than the monovalent metal, it combines in a ratio of more than 1:1 depending on the valency of the metal.

The compound of formula (1) according to the present invention can exist as a stereoisomer, and thus, the present invention also includes each of the stereoisomers and their mixtures including racemate. Among the stereoisomers, compounds wherein the configuration of 3- and 4-position chiral carbons in the chromane(or thiochromane) ring is (3R, 4R) or (3S, 4S) or mixtures thereof are preferable, and in this case, compounds wherein the chiral carbon in the 4-position side chain of chromane(or thiochromane) ring, to which $R^1OOC$— group is attached, has the configuration of R or S or mixtures thereof are preferable.

As the pharmaceutically acceptable salts of the compound of formula (1), the metal salts as described above, for example, sodium, potassium, calcium salt, etc. can be mentioned. These salts may be prepared according to the conventional conversion methods.

Among the compound of formula (1), the preferred compounds include those wherein $R^1$ is hydrogen, X is oxygen or sulfur, and m is an integer of 6 to 10, particularly preferably an integer of 8 or 9.

As typical examples of the compound of formula (1), the following compounds can be mentioned:

(3'RS,4'RS)-10-[7-hydroxy-3-(4-hydroxyphenyl)-3-methylthiochroman-4-yl]-2-(7,7,8,8,8-pentafluorooctyl) decanoic acid;

(3'RS,4'RS)-11-[7-hydroxy-3-(4-hydroxyphenyl)-3-methylthiochroman-4-yl]-2-(7,7,8,8,8-pentafluorooctyl) undecanoic acid;

(3'RS,4'RS)-11-[7-hydroxy-3-(4-hydroxyphenyl)-3-methylchroman-4-yl]-2-(7,7,8,8,8-pentafluorooctyl) undecanoic acid; and (3'RS,4'RS)-10-[7-hydroxy-3-(4-hydroxyphenyl)-3-methylchroman-4-yl]-2-(7,7,8,8,8-pentafluorooctyl) decanoic acid.

The compound of formula (1) according to the present invention can be prepared by the following Processes I to V, and thus, the present invention also provides these processes.

(Process I)

The compound of formula (1) can be prepared by a process characterized in that (a) a compound of the following formula (2):

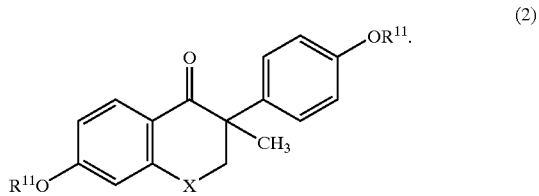

in which
X is defined as previously described, and
$R^{11}$ represents hydroxy- or carboxy-protecting group, preferably t-butyldimethylsilyl, triisopropylsilyl, triethylsilyl, t-butyldiphenylsilyl, methoxymethyl, tetrahydropyranyl, methyl, ethyl, etc., is reacted with an acetylene compound of the following formula (3):

in which $m_1$ represents a number of m-2, and $R^{12}$ represents hydroxy- or carboxy-protecting group, preferably t-butyldimethylsilyl, triisopropylsilyl, triethylsilyl, t-butyldiphenylsilyl, methoxymethyl, tetrahydropyranyl, methyl, ethyl, etc., in an inert solvent in the presence of a base to give a compound of the following formula (4):

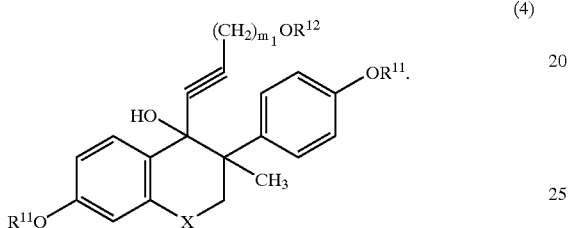

in which X, $m_1$, $R^{11}$ and $R^{12}$ are defined as previously described (where tetrahydrofuran, dioxane, dichloromethane or chloroform, preferably tetrahydrofuran or dioxane is used as the inert solvent; n-butyllithium, sec-butyllithium or sodium hydride is used as the base; and the reaction is carried out at temperatures ranging from −78° C. to the boiling point of the reaction mixture, preferably from −78° C. to room temperature);

(b) the compound of formula (4) is reduced by sodium cyanoborohydride in an inert solvent in the presence of a Lewis acid to give a compound of the following formula (5):

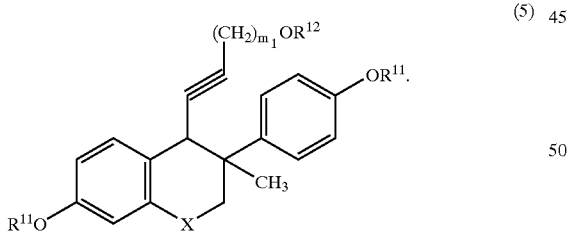

in which X, $m_1$, $R^{11}$ and $R^{12}$ are defined as previously described (where tetrahydrofuran, dioxane, dichloromethane, dichloroethane, or chloroform, preferably dichloroethane is used as the inert solvent; zinc iodide is used as the Lewis acid; and the reaction is carried out at temperatures ranging from −78° C. to the boiling point of the reaction mixture, preferably from 0° C. to room temperature);

(c) the compound of formula (5) is subjected to a catalytic hydrogenation reaction in an inert solvent and optionally in the presence of sodium hydrogen carbonate to give a compound of the following formula (6):

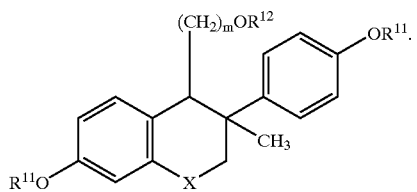

in which X, m, $R^{11}$ and $R^{12}$ are defined as previously described (where methanol, ethanol, ethyl acetate, tetrahydrofuran, dioxane, dichloromethane, dichloroethane, or chloroform, preferably tetrahydrofuran or ethyl acetate is used as the inert solvent; activated Pd/C, palladium hydroxide or platinum oxide is used as the catalyst; and the reaction is carried out at temperatures ranging from room temperature to the boiling point of the reaction mixture, preferably at room temperature), however, the compound of formula (6) may be directly obtained from the compound of formula (4) through a catalytic hydrogenation reaction in an inert solvent (where the reaction conditions are the same as the step of preparing the compound of formula (6) from the compound of formula (5));

(d) the hydroxy group in the compound of formula (6) is deprotected by the treatment with one or more substances selected from a group consisting of tetrabutylammonium fluoride, cesium fluoride, hydrofluoride-pyridine, hydrochloride, sulfuric acid and p-toluenesulfonic acid in an inert solvent to give a compound of the following formula (7):

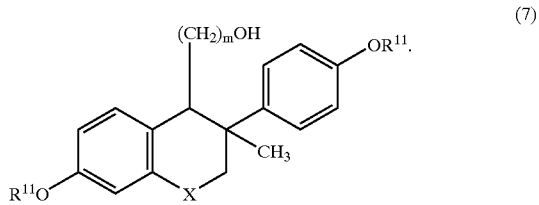

in which X, m, and $R^{11}$ are defined as previously described (where tetrahydrofuran, dioxane, dichloromethane, dichloroethane, or chloroform, preferably tetrahydrofuran is used as the inert solvent; and the reaction is carried out at temperatures ranging from room temperature to the boiling point of the reaction mixture);

(e) the compound of formula (7) is treated with methyl sulfonyl chloride or p-toluene sulfonyl chloride in an inert solvent in the presence of an organic base to convert the group of $(CH_2)_mOH$ in compound (7) to a group of $(CH_2)_mO-SO_2CH_3$ or $(CH_2)_mO-SO_2-C_6H_4-p-CH_3$ (where tetrahydrofuran, dioxane, dichloromethane, dichloroethane, or chloroform, preferably dichloromethane is used as the inert solvent; triethylamine or pyridine is used as the organic base; and the reaction is carried out at temperatures ranging from room temperature to the boiling point of the reaction mixture, preferably at room temperature), or the resulting compound is further treated with metal halide in an inert solvent to give a compound of the following formula (8):

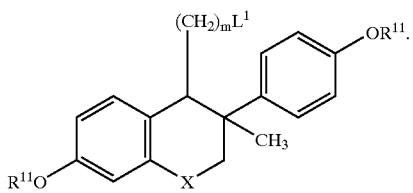

(8)

in which

X, m, and $R^{11}$ are defined as previously described, and
$L^1$ represents a leaving group, preferably methanesulfonyloxy, p-toluenesulfonyloxy, halogen, etc. (where acetone, tetrahydrofuran, dioxane, dichloromethane, dichloroethane or chloroform, preferably dichloromethane is used as the inert solvent; sodium iodide or potassium iodide is used as the metal halide; and the reaction is carried out at temperatures ranging from room temperature to the boiling point of the reaction mixture, preferably at the boiling point of the reaction mixture);

(f) the compound of formula (8) is reacted with a malonate of the following formula (9):

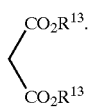

(9)

in which $R^{13}$ represents hydroxy- or carboxy-protecting group, preferably t-butydimethylsilyl, triisopropylsilyl, triethylsilyl, t-butyldiphenylsilyl, methoxyrethyl, tetrahydropyranyl, methyl, ethyl, etc., in an inert solvent in the presence of a base to give a compound of the following formula (10):

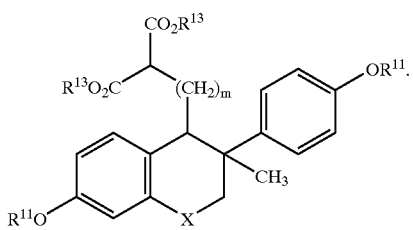

(10)

in which X, m, $R^{11}$ and $R^{13}$ are defined as previously described (where tetrahydrofuran, dioxane, dimethylsulfoxide, dichloromethane, dichloroethane or chloroform, preferably tetrahydrofuran is used as the inert solvent; sodium hydride, sodium hydroxide or potassium t-butoxide is used as the base; and the reaction is carried out at temperatures ranging from room temperature to the boiling point of the reaction mixture);

(g) the compound of formula (10) is reacted with a compound of the following formula (11):

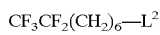

(11).

in which $L^2$ represents a leaving group, preferably methanesulfonyloxy, p-toluenesulfonyloxy, halogen, etc., in an inert solvent in the presence of a base to give a compound of the following formula (12):

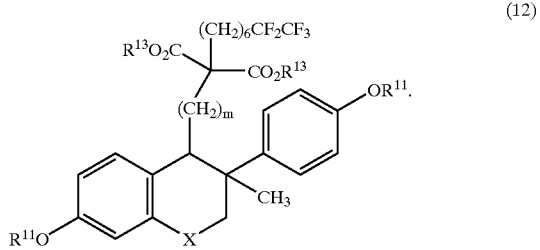

(12)

in which X, m, $R^{11}$ and $R^{13}$ are defined as previously described (where the reaction conditions are the same as step (f));

(h) the compound of formula (12) is treated with sodium hydroxide or potassium hydroxide in an inert solvent to give a compound of the following formula (13):

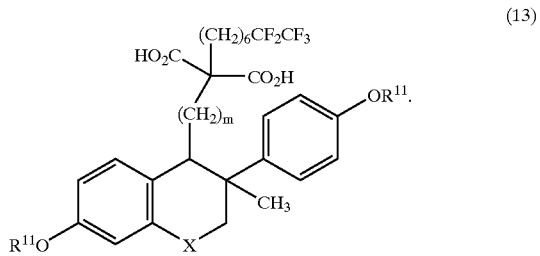

(13)

in which X, m and $R^{11}$ are defined as previously described (where water, ethanol, methanol, water-ethanol or water-methanol mixture is used as the inert solvent; and the reaction is carried out at temperatures ranging from room temperature to the boiling point of the reaction mixture, preferably at the boiling point of the reaction mixture);

(i) the compound of formula (13) is heated to a temperature of from 50° C. to the boiling point of the reaction mixture in an inert solvent and optionally in the presence of an acid to give a compound of the following formula (14):

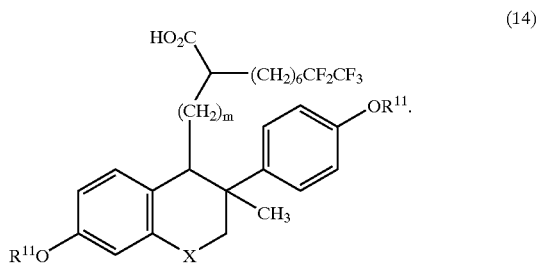

(14)

in which X, m and $R^{11}$ are defined as previously described (where dimethylsulfoxide, dimethylformamide, benzene, toluene, xylene, dioxane or tetrahydrofuran is used as the inert solvent; and hydrochloric acid, sulfuric acid or p-toluenesulfonic acid is used as the acid); and (j) the compound of formula (14) is deprotected by an acid to give a compound of the following formula (1a):

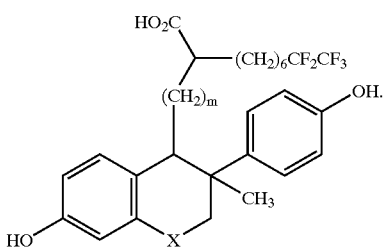

(1a)

in which X and m are defined as previously described (where hydrochloric acid, sulfuric acid, hydrobromic acid, hydrogen pyridinium chloride or borontribromide is used as the acid; and the reaction is carried out at temperatures ranging from −78° C. to the boiling point of the reaction mixture); or (k) the compound of formula (1a) is treated with a compound of the following formula (15):

 (15).

in which
$R^{1'}$ represents a metal, and
$L^3$ represents hydroxy, alkylcarbonyloxy, lower alkoxy, etc., to give a metal salt compound of the following formula (1b):

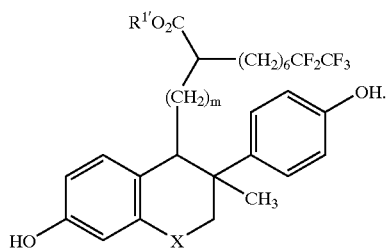

(1b)

in which X, m and $R^{1'}$ are defined as previously described.

(Process II)

The compound of formula (1) can also be prepared by a process characterized in that the compound of formula (13) obtained in step (h) of Process I is reacted according to the same procedure as step (j) to give a compound of the following formula (16):

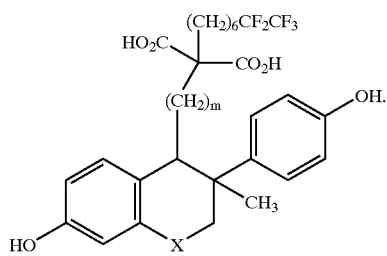

(16)

in which X and m are defined as previously described, the resulting compound (16) is reacted according to the same procedure as step (i) to give the compound of formula (1a), which may be further converted to a metal salt thereof according to the same procedure as step (k) to give the compound of formula (1b). That is, Process II produces the compound of formula (1) in the same manner as Process I except that the order of decarboxylation and deprotection of group $R^{11}$ is reversed. And the reaction conditions are the same.

(Process III)

The compound of formula (1) can also be prepared by a process characterized in that the compound of formula (8) obtained in step (e) of Process I is reacted with a compound of the following formula (17):

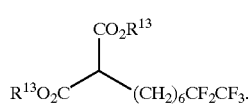

(17)

in which $R^{13}$ is defined as previously described, in an inert solvent in the presence of a base to give the compound of formula (12) (where tetrahydrofuran, dioxane, dichloromethane, dichloroethane or chloroform, preferably tetrahydrofuran is used as the inert solvent; sodium hydride, sodium hydroxide or potassium t-butoxide is used as the base; and the reaction is carried out at temperatures ranging from −78° C. to the boiling point of the reaction mixture) and the subsequent reactions are carried out according to the same procedure as Process I or II.

(Process IV)

The compound of formula (1) can also be prepared by a process characterized in that (a) a compound of the following formula (18):

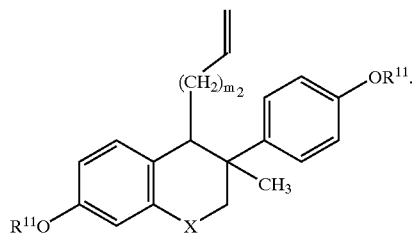

(18)

in which
X and $R^{11}$ are defined as previously described, and
$m_2+m_3+2$ equals m, is reacted with a compound of the following formula (19):

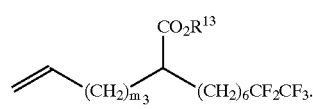

(19)

in which $m_3$ and $R^{13}$ are defined as previously described, in an inert solvent in the presence of a catalyst to give a compound of the following formula (20):

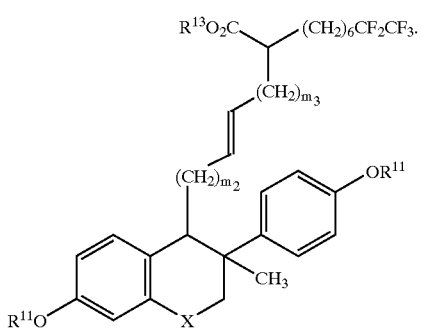

(20)

in which X, $R^{11}$, $R^{13}$, $m_2$ and $m_3$ are defined as previously described (where methylene chloride, chloroform, benzene, toluene, xylene, dioxane, tetrahydrofuran, dimethylsulfoxide or dimethylformamide is used as the inert solvent; benzylidene-bis (tricyclohexylphosphine)dichlororuthenium is used as the catalyst; and the reaction is carried out at temperatures ranging from −78° C. to the boiling point of the reaction mixture, preferably at the boiling point of the reaction mixture); and (b) the compound of formula (20) is subjected to a catalytic hydrogenation reaction in an inert solvent to give a compound of the following formula (21):

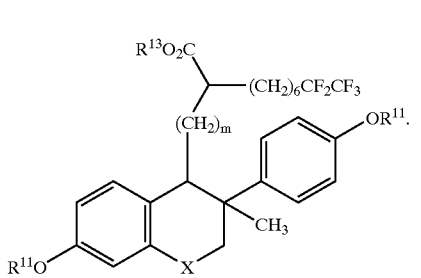

(21)

in which X, m, $R^{11}$ and $R^{13}$ are defined as previously described (where methanol, ethanol, ethyl acetate, tetrahydrofuran, dioxane, dichloromethane, dichloroethane, chloroform or benzene is used as the inert solvent; activated Pd/C, palladium hydroxide, platinum oxide or Wilkinson's catalyst is used as the catalyst; and the reaction is carried out at temperatures ranging from room temperature to the boiling point of the reaction mixture, preferably at room temperature) ), and then hydrolysis, deprotection and conversion to the metal salt thereof are carried out according to the same procedure as Process I or II.

(Process V)

The compound of formula (1) can also be prepared by a process characterized in that (a) the compound of formula (18) is reacted with a compound of the following formula (22):

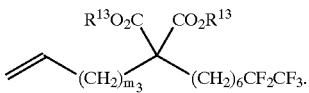

(22)

in which $R^{13}$ and $m_3$ are defined as previously described, in an inert solvent in the presence of a catalyst to give a compound of the following formula (23):

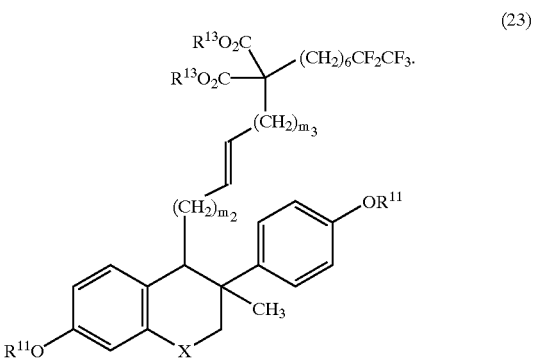

(23)

in which X, $R^{11}$, $R^{13}$, $m_2$ and $m_3$ are defined as previously described (where the reaction conditions are the same as step (a) of Process IV); and (b) the compound of formula (23) is subjected to a catalytic hydrogenation reaction in a solvent to give a compound of the following formula (24):

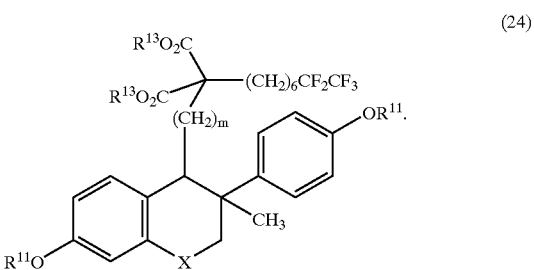

(24)

in which X, $R^{11}$, $R^{13}$ and m are defined as previously described (where the reaction conditions are the same as step (b) of Process IV), and then hydrolysis, decarboxylation, deprotection and conversion to the metal salt thereof are carried out according to the same procedure as Process I or II.

The compound of formula (1) thus prepared may be separated and purified using the conventional methods, such as for example, column chromatography, recrystallization, etc.

The above processes I to V according to the present invention will be more specifically explained through the following examples.

As stated above, the compound of formula (1) prepared according to the processes as explained above has a good anti-estrogenic activity and therefore, can be used for the treatment of estrogen-related diseases including anovular infertility, breast cancer, endometrial cancer, uterine cancer, ovarian cancer, endometriosis, endometrial fibroma, benign prostate hypertrophy, premature, menstrual disorder, etc.

Therefore, the present invention relates to an anti-estrogenic pharmaceutical composition comprising the compound of formula (1) as an active component together with pharmaceutically acceptable carriers.

When the anti-estrogenic pharmaceutical composition containing the compound of the present invention as an active component is used for clinical purpose, it can be formulated into a conventional preparation in the pharmaceutical field, for example, preparation for oral administration such as tablet, capsule, troche, solution, suspension, etc., or injectable preparation such as injectable solution or suspension, ready-to-use injectable dry powder which can be reconstituted with distilled water for injection when it is injected, etc., by combining with carriers conventionally used in the pharmaceutical field.

Suitable carrier which can be used in the composition of the present invention includes those conventionally used in the pharmaceutical field, for example, binder, lubricant, disintegrant, excipient, solubilizer, dispersing agent, stabilizing agent, suspending agent, coloring agent, perfume, etc. for oral preparation; and preservative, pain alleviating agent, solubilizing agent, stabilizing agent, etc. for injectable preparation. The pharmaceutical preparation thus prepared can be administered orally or parenterally, for example, intravenously, subcutaneously or intraperitoneally. In addition, in order to prevent the active component from being decomposed with gastric acid, the oral preparation can be administered together with an antacid or in the enteric-coated form of the solid preparation such as tablet.

The dosage of the 3-methyl-chromane or thiochromane derivative of formula (1) for human being can be suitably determined depending on absorption, inactivation and secretion of the active ingredient in the human body, age, sex and condition of subject patient, severity of the disease to be treated. It is generally suitable to administer the compound of formula (1) in an amount of 0.1 to 500 mg/day when it is orally administered, and in an amount of 1 to 1000 mg/month when it is parenterally administered (intravenous, intramuscular, or subcutaneous injection) for adult patient.

The present invention is more specifically explained by the following examples. However, it should be understood that the present invention is not limited to these examples in any manner.

EXAMPLE 1

Synthesis of (3'RS,4'RS)-10-[7-hydroxy-3-(4-hydroxyphenyl)-3-methylthiochroman-4-yl]-2-(7,7,8,8,8-pentafluorooctyl)decanoic Acid (Step 1) 1-Methylsulfonyloxy-7,7,8,8,8-pentafluorooctane

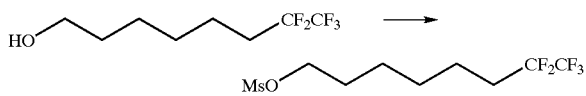

7,7,8,8,8-Pentafluorooctan-1-ol(25 g, 113 mmol) was dissolved in dichloromethane (250 ml), triethylamine(47.4 ml, 339 mmol) and methanesulfonylchloride(17.6 ml, 227 mmol) were added dropwise under cooling to 0° C., and the resulting mixture was stirred for 1 hour. The reaction solution was diluted with water, extracted twice with dichloromethane(200 ml), washed with water and saturated saline solution, dried over anhydrous magnesium sulfate, and filtered. The filtrate was concentrated under reduced pressure and the residue was purified by silica gel column chromatography (eluent:ethyl acetate/n-hexane=1/10, v/v) to give 30 g(100 mmol, Yield 89%) of the title compound.

$^1$H-NMR(300 MHz, CDCl$_3$): δ4.24(t, 2H), 3.01(s, 3H), 2.13-1.96(m, 2H), 1.85-1.76(m, 2H), 1.70-1.47(m, 6H)

(Step 2) 1,1,1,2,2-Pentafluoro-8-iodooctane

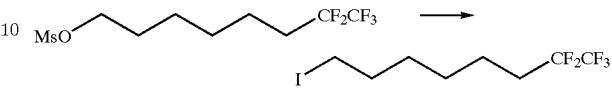

1-Methylsulfonyloxy-7,7,8,8,8-pentafluorooctane(14 g, 47.01 mmol) prepared in Step 1 was dissolved in acetone (200 ml), sodium iodide(19.62 g, 130 mmol) was added thereto, and the resulting mixture was stirred overnight under reflux-heating condition. The reaction solution was diluted with excess water(1 l), extracted twice with diethylether (100 ml), washed with 1% aqueous sodiumthiosulfate solution(100 ml) and saturated saline solution, dried over anhydrous magnesium sulfate, and filtered. The filtrate was concentrated under reduced pressure to give 14 g(42 mmol, Yield 89%) of the title compound.

$^1$H-NMR(300 MHz, CDCl$_3$): δ3.15(t, 2H), 2.00(m, 2H), 1.80(m, 2H), 1.60(m, 2H), 1.38(m, 4H)

(Step 3) Dimethyl 2-hept-6-enylpropan-1,3-dioate

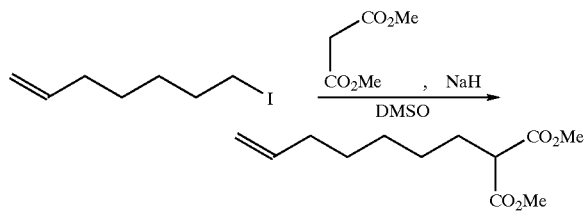

Dimethylmalonate(8.16 ml, 71.4 mmol) was dissolved in anhydrous DMSO(60 ml), 60% sodium hydride(1.29 g, 53.55 mmol) was added thereto at 0° C., and the resulting mixture was stirred for 30 minutes at room temperature. To the reaction mixture was added 7-iodohept-1-ene(8.0 g, 35.70 mmol), which was then stirred under heating at 60~70° C. for 4 hours. The temperature was lowered to 0° C. and water was added. The mixture thus obtained was extracted with ethyl acetate, washed with water and saturated saline solution in order, dried over anhydrous magnesium sulfate, and concentrated under reduced pressure. The residue was purified by column chromatography (eluent:n-hexane/ethyl acetate=40/1, v/v) to give 7.1 g(Yield 87.1%) of the pure title compound as a colorless oil.

$^1$H-NMR (300 MHz, CDCl$_3$): δ5.73(m, 1H), 5.00-4.80(m, 2H), 3.70(s, 3H), 3.65(s, 3H), 3.31(m, 1H), 2.04-1.92(m, 2H), 1.92-1.78(m, 2H), 1.42-1.12(m, 6H)

(Step 4) Dimethyl 2-hept-6-enyl-2-(7,7,8,8,8-pentafluorooctyl)propan-1,3-dioate

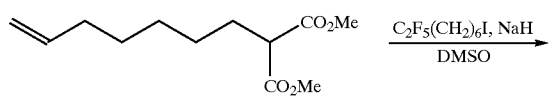

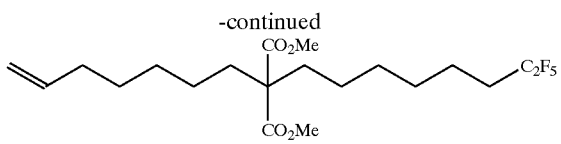

Dimethyl 2-hept-6-enylpropan-1,3-dioate(5 g, 21.9 mmol) prepared in Step 3 was dissolved in anhydrous DMSO(50 ml), 60% sodium hydride(0.96 g, 24.09 mmol) was added at room temperature, and the resulting mixture was stirred for 30 minutes at room temperature. To the reaction mixture was added 1,1,1,2,2-pentafluoro-8-iodooctane(8.7 g, 26.28 mmol) prepared in Step 2, which was then stirred overnight under heating at 70~80° C. The temperature was lowered to 0° C. and water was added. The mixture thus obtained was extracted with ethyl acetate, washed with water and saturated saline solution in order, dried over anhydrous magnesium sulfate, and concentrated under reduced pressure. The residue was purified by column chromatography(eluent:n-hexane/ethyl acetate=30/1, v/v) to give 9.3 g(Yield 98.8%) of the pure title compound as a colorless oil.

$^1$H-NMR (300 MHz, CDCl$_3$): δ5.88(m, 1H), 5.10-4.95(m, 2H), 3.72(s, 6H), 2.15-1.80(m, 8H), 1.72-1.40(m, 14H)

(Step 5) Methyl 2-(7,7,8,8,8-pentafluorooctyl)-8-nonenoate

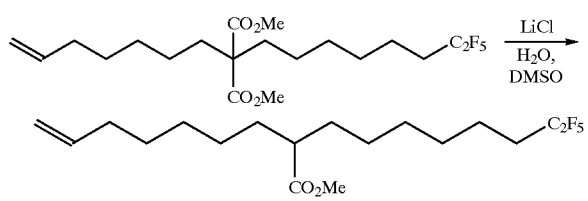

Dimethyl 2-hept-6-enyl-2-(7,7,8,8,8-pentafluorooctyl)propan-1,3-dioate(9.31 g, 21.62 mmol) prepared in Step 4 was dissolved in anhydrous DMSO(100 ml), water(0.39 ml, 21.62 mmol) and lithium chloride(1.82 g, 43.25 mmol) were added, and the resulting mixture was stirred for 4 hours at 180° C. The reaction mixture was cooled to room temperature, extracted with ethyl acetate, washed with distilled water, and dried over anhydrous magnesium sulfate. The solvent was removed by concentration under reduced pressure and the residue was purified by column chromatography(eluent:n-hexane/ethyl acetate=50/1, v/v) to give 4.46 g(Yield 55.4%) of the title compound as a colorless oil.

$^1$H-NMR (300 MHz, CDCl$_3$): δ5.83(m, 1H), 5.10-4.86(m, 2H), 3.70(s, 3H), 2.32(m, 1H), 2.18-1.86(m, 4H), 1.80-1.15 (m, 18H)

(Step 6) (3RS,4RS)-4-allyl-7-methoxy-3-(4-methoxyphenyl)-3-methylthiochromane

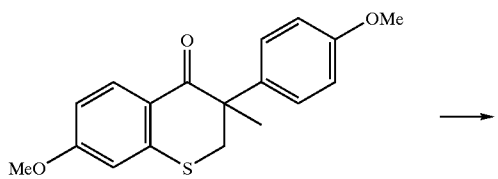

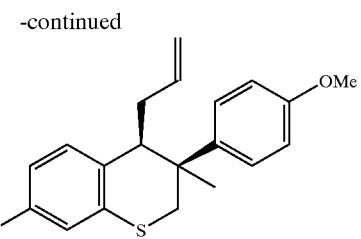

7-Methoxy-3-(4-methoxyphenyl)-3-methylthiochroman-4-one(2.24 g, 6.823 mmol) prepared according to the known method in WO98/25916 was dissolved in dry tetrahydrofuran(30 ml) and then cooled to −78° C. Lithium aluminum hydride(1N solution in THF, 3.41 ml, 3.412 mmol) was added dropwise thereto and the resulting mixture was stirred overnight at room temperature. The reaction mixture was treated with saturated aqueous ammonium chloride solution(100 ml), extracted twice with ethyl acetate (100 ml), washed with water and saturated saline solution, dried over anhydrous magnesium sulfate, and filtered. The filtrate was concentrated under reduced pressure and the residue was dissolved in 1,2-dichloroethane(30 ml). Zinc iodide(2.61 g, 8.188 mmol) and allyltrimethylsilane(2.17 ml, 13.646 mmol) were added dropwise thereto under cooling to 0° C. and the resulting mixture was stirred overnight at room temperature. The reaction mixture was diluted with water(200 ml), extracted twice with dichloromethane(200 ml), washed with water and saturated saline solution, dried over anhydrous magnesium sulfate, and filtered. The filtrate was concentrated under reduced pressure and the residue thus obtained was purified by silica gel column chromatography(eluent:ethyl acetate/n-hexane=1/4, v/v) to give 1.4 g(Yield 58%) of the title compound.

$^1$H-NMR(300 MHz, CDCl$_3$): δ7.27(d, 2H, J=7.2 Hz), 6.91-6.87(m, 3H), 6.71 (d, 1H), 6.55(dd, 1H, J$_1$=8.9 Hz, J$_2$=2.4 Hz), 5.56(m, 1H), 4.85(d, 1H, J=9.8 Hz), 4.66(d, 1H J=17.0 Hz), 3.81(s, 3H), 3.76(s, 3H), 3.6(d, 1H, J=12.1 Hz), 2.98(d, 1H, J=12.1 Hz), 2.90(m, 1H), 1.96-1.82(m, 2H), 1.2(s, 3H)

(Step 7) (3'RS,4'RS)-methyl 10-[7-methoxy-3-(4-methoxyphenyl)-3-methylthiochroman-4-yl]-2-(7,7,8,8,8-pentafluorooctyl)-8-decenoate

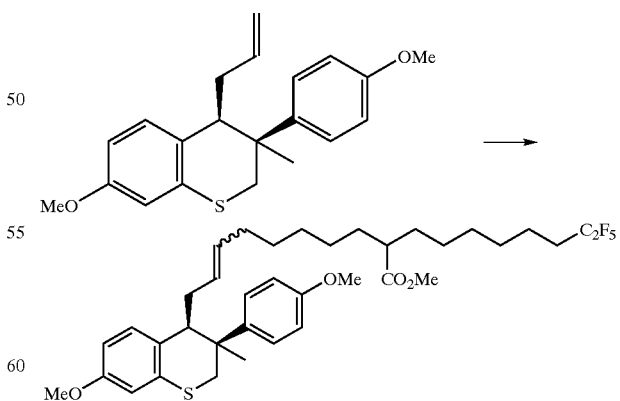

(3RS,4RS)-4-allyl-7-methoxy-3-(4-methoxyphenyl)-3-methylthiochromane(200 mg, 0.587 mmol) prepared in Step 6 was dissolved in dichloromethane(20 ml), methyl 2-(7,7,8,8,8-pentafluorooctyl)-8-nonenoate(0.44 g, 1.175 mmol)

prepared in Step 5 and benzylidene-bis(tricyclohexylphosphine)dichlororuthenium(24 mg, 0.03 mmol) were added thereto, and the resulting mixture was stirred under reflux overnight. The reaction mixture was concentrated under reduced pressure and the residue thus obtained was purified by column chromatography(eluent:n-hexane/ethyl acetate=30/1, v/v) to give 270 mg(Yield 67.1%) of the pure title compound having a pale yellow color.

$^1$H-NMR (300 MHz, CDCl$_3$): δ7.42-7.25(m, 2H), 7.02-6.85(m, 3H), 6.71-6.65(m, 1H), 6.60-6.50(m, 1H), 5.40-4.92 (m, 2H), 4.00-3.60(m, 10H), 3.08-2.92 (m, 1H), 2.75(m, 1H), 2.40-2.25(m, 1H), 2.18-0.80(m, 27H)

(Step 8) (3'RS,4'RS)-methyl 10-[7-methoxy-3-(4-methoxyphenyl)-3-methylthiochroman-4-yl]-2-(7,7,8,8,8-pentafluorooctyl)decanoate (3'RS,4'RS)-methyl 10-[7-methoxy-3-(4-methoxyphenyl)-3-methylthiochroman-4-yl]-2-(7,7,8,8,8-pentafluorooctyl)-8-decenoate(270 mg, 0.394 mmol) was dissolved in tetrahydrofuran(20 ml), 10% Pd/C(55 mg) was added, and the resulting mixture was stirred overnight under hydrogen atmosphere. The reaction mixture was filtered through cellite and the filtrate was concentrated under reduced pressure to give 255 mg(Yield 94.2%) of the pure title compound.

$^1$H-NMR (300MHz, CDCl$_3$): δ7.30(d, 2H), 6.92(t, 3H), 6.72(d, 1H), 6.65-6.50(m, 1H), 3.79(s, 3H), 3.78(s, 3H), 3.70-3.58(m, 4H), 3.00(d, 1H), 2.70(bd, 1H), 2.40-2.20(m, 1H), 2.10-1.86(m, 4H), 1.76-0.84(m, 27H)

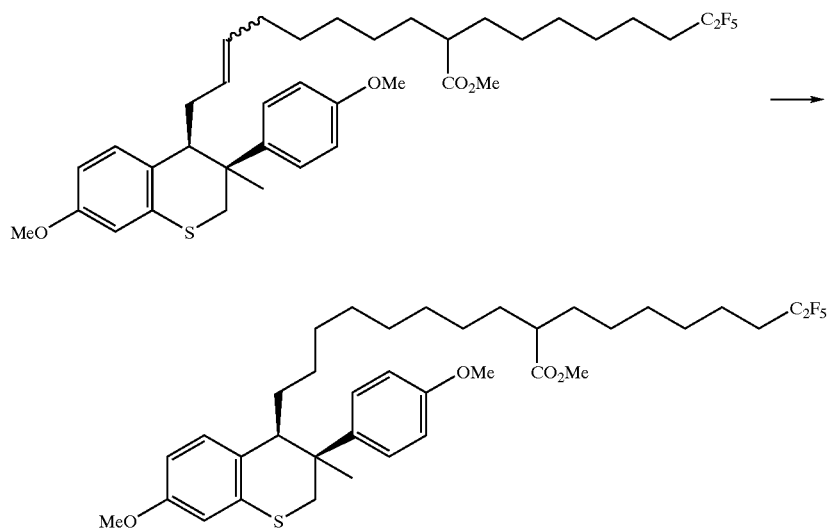

(Step 9) (3'RS,4'RS)-10-[7-hydroxy-3-(4-hydroxyphenyl)-3-methylthiochroman-4-yl]-2-(7,7,8,8,8-pentafluorooctyl)decanoic acid

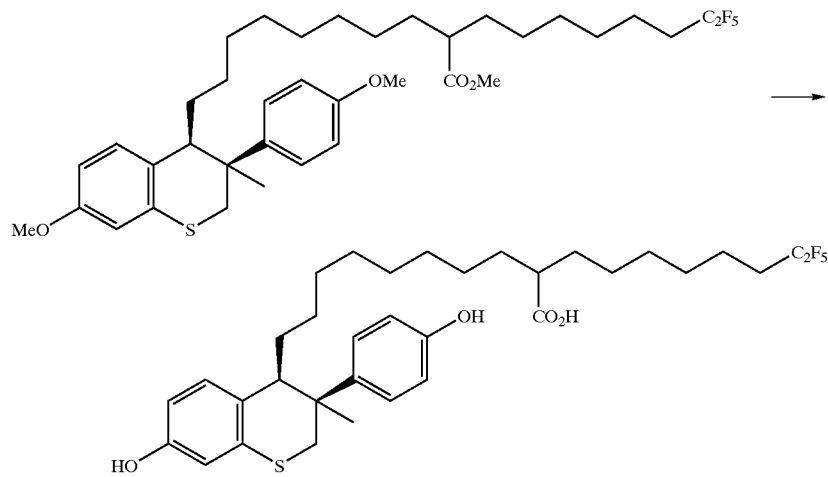

(3'RS,4'RS)-methyl 10-[7-methoxy-3-(4-methoxyphenyl)-3-methylthiochroman-4-yl]-2-(7,7,8,8,8-pentafluorooctyl)decanoate(255 mg, 0.371 mmol) was dissolved in dichloromethane(5 ml) and cooled down to −78° C. Borontribromide(2.23 ml, 2.23 mmol) was added thereto and the resulting mixture was stirred for 2 hours at −10° C. and for 6 hours at 0~5° C. To the reaction mixture was added ice water. The resulting mixture was extracted with dichloromethane, washed with 1% sodiumthiosulfate solution and saturated saline solution, and dried over anhydrous magnesium sulfate. The solution was concentrated under reduced pressure to remove the organic solvent and the residue thus obtained was purified by MPLC(Medium Pressure Liquid Chromatography; eluent:methanol/water=4/1→5.5/1, column: RP-18) to give 45 mg(Yield 18.8%) of the pure title compound as an oil.

$^1$H-NMR (300 MHz, MeOH-d$_4$): δ7.24(d, J=8.5 Hz, 2H), 6.81(dd, J$_1$=8.4 Hz, J$_2$=2.3 Hz, 3H), 6.56(d, J=2.3 Hz, 1H), 6.45-6.42(m, 1H), 3.61(d, J=11.7 Hz, 1H), 2.95(d, J=11.7 Hz, 1H), 2.73(bs, 1H), 2.38-1.99(m, 3H), 1.90-0.92(m, 29H)

EXAMPLE 2

Synthesis of (3'RS,4'RS)-11-[7-hydroxy-3-(4-hydroxyphenyl)-3-methylthiochroman-4-yl]-2-(7,7,8,8,8-pentafluorooctyl)undecanoic acid (Step 1) Dimethyl 2-oct-7-enyl-2-(7,7,8,8,8-pentafluorooctyl)propan-1,3-dioate

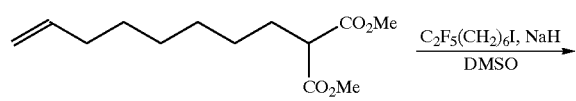

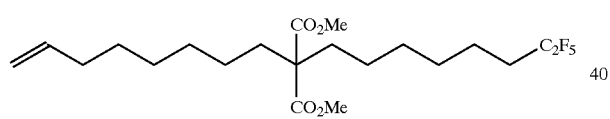

The title compound was prepared according to the same procedure as Step 4 of Example 1.

$^1$H-NMR (300 MHz, CDCl$_3$): δ5.95-5.70(m, 1H), 5.10-4.86(m, 2H), 3.75(s, 6H), 2.20-1.80(m, 8H), 1.78-1.04(m, 16H)

(Step 2) Methyl 2-(7,7,8,8,8-pentafluorooctyl)-9-decenoate

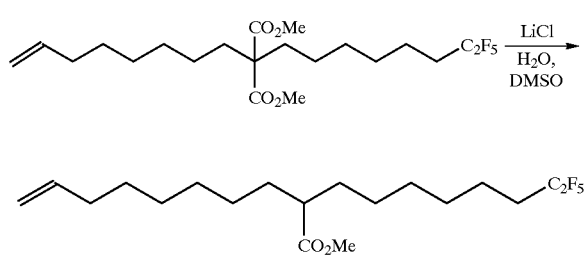

The title compound was prepared according to the same procedure as Step 5 of Example 1.

$^1$H-NMR (300 MHz, CDCl$_3$): δ5.90-5.71(m, 1H), 5.08-4.88(m, 2H), 3.70(s, 3H), 2.40-2.22(m, 1H), 2.14-1.85(m, 4H), 1.78-1.16(m, 20H)

(Step 3) (3'RS,4'RS)-methyl 11-[7-methoxy-3-(4-methoxyphenyl)-3-methylthiochroman-4-yl]-2-(7,7,8,8,8-pentafluorooctyl)-9-undecenoate

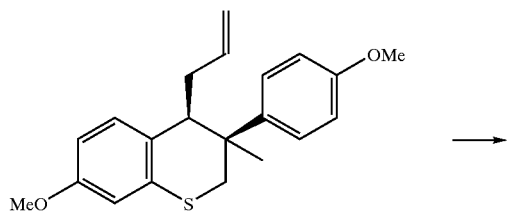

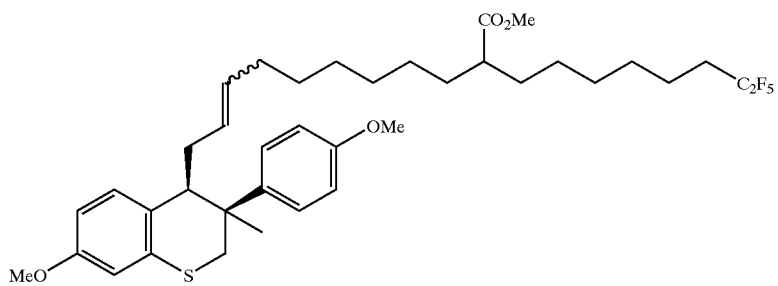

The title compound was prepared according to the same procedure as Step 7 of Example 1.

¹H-NMR (300 MHz, CDCl₃): δ7.40-7.26(m, 2H), 7.00-6.82(m, 3H), 6.76-6.68 (m, 1H), 6.60-6.48(m, 1H), 5.40-4.90(m, 2H), 4.00-3.60(m, 10H), 3.04-2.94 (m, 1H), 2.84-2.70(m, 1H), 2.40-2.25(m, 1H), 2.10-0.98(m, 29H)

(Step 4) (3'RS,4'RS)-methyl 11-[7-methoxy-3-(4-methoxyphenyl)-3-methylthiochroman-4-yl]-2-(7,7,8,8,8-pentafluorooctyl)undecanoate The title compound was prepared according to the same procedure as Step 8 of Example 1.

¹H-NMR (300 MHz, CDCl₃): δ7.30(d, 2H), 6.92(m, 3H), 6.72(d, 1H), 6.65-6.50(m, 1H), 3.79(s, 3H), 3.75(s, 3H), 3.70-3.58(m, 4H), 3.00(d, 1H), 2.70(m, 1H), 2.40-2.20(m, 1H), 2.10-1.86(m, 4H), 1.76-0.84(m, 29H)

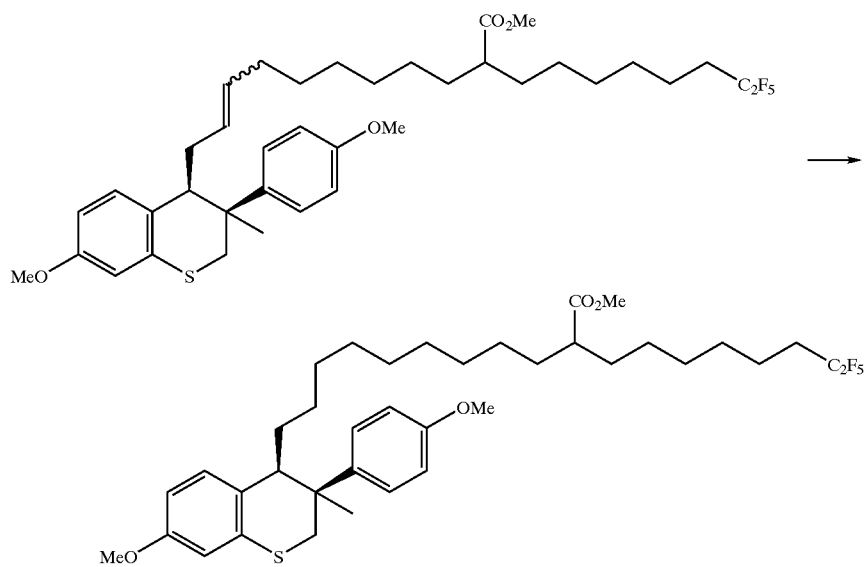

(Step 5) (3'RS,4'RS)-11-[7-hydroxy-3-(4-hydroxyphenyl)-3-methylthiochroman-4-yl]-2-(7,7,8,8,8-pentafluorooctyl)undecanoic acid

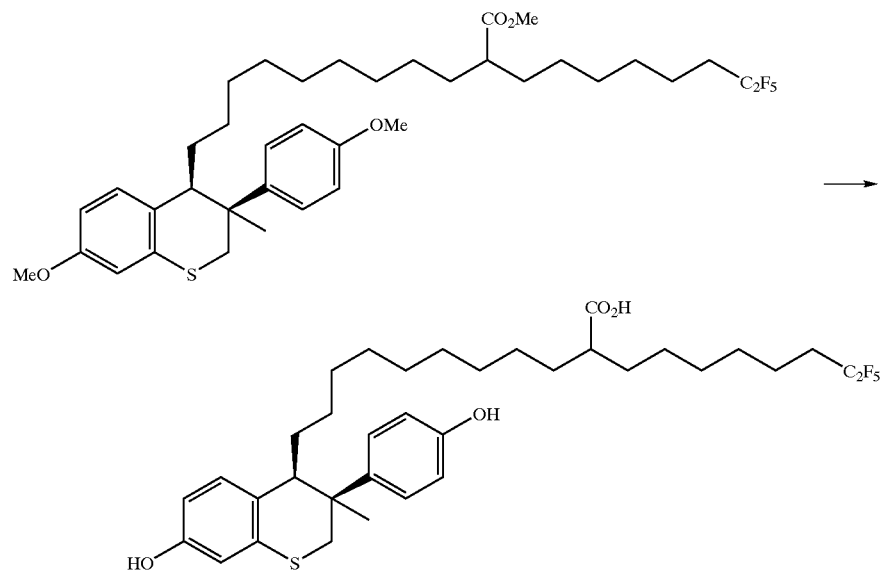

The title compound was prepared according to the same procedure as Step 9 of Example 1.

¹H-NMR (300 MHz, CDCl₃): δ7.24-7.20(m, 2H), 6.84(m, 3H), 6.67(d, J=2.5 Hz, 1H), 6.50(dd, J₁=8.1 Hz, J₂=2.5 Hz, 1H), 3.66(d, J=11.5 Hz, 1H), 2.96 (d, J=11.5 Hz, 1H), 2.70(bs, 1H), 2.10-1.90(m, 2H), 1.70-0.90(m, 31H)

EXAMPLE 3

Synthesis of (3'RS,4'RS)-11-[7-hydroxy-3-(4-hydroxyphenyl)-3-methylchroman-4-yl]-2-(7,7,8,8,8-pentafluorooctyl)undecanoic acid (Step 1) 7-Methoxymethoxy-3-(4-methoxymethoxyphenyl)-3-methylchroman-4-one

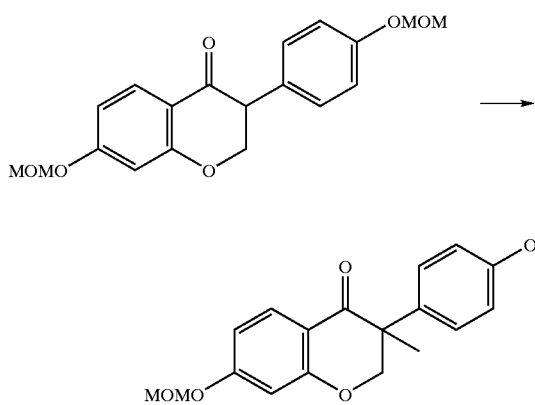

7-Methoxymethoxy-3-(4-methoxymethoxyphenyl)chroman-4-one(57.4 g, 0.167 mol) (see, Helv. Chim. Acta., 75, 2, 1992, 457-470) was dissolved in acetone(1100 ml), potassium carbonate(230 g, 1.67 mol) and methyl iodide (104 ml, 1.67 mol) were added thereto in order, and the resulting mixture was stirred for 5 days at room temperature. The reaction mixture was diluted with ethyl acetate and washed with water. The organic layer thus obtained was dried over magnesium sulfate, filtered, and concentrated under reduced pressure. The residue was purified by column chromatography(eluent:n-hexane/ethyl acetate=8/1, v/v) to give the title compound(49.2 g, Yield 82%) as a colorless oil.

¹H-NMR(300 MHz, CDCl₃): δ7.83(d, 1H, J=8.8 Hz), 7.29(d, 2H, J=8.5 Hz), 6.93(d, 2H, J=8.5 Hz), 6.61(dd, 1H, J=8.5 Hz, J=2.2 Hz), 6.49(d, 1H, J=2.3 Hz), 5.12(s, 2H), 5.08(s, 2H), 4.77(d, 1H, J=12.2 Hz), 4.28(d, 1H, J=12.2 Hz), 3.41(s, 3H), 3.40(s, 3H), 1.40(s, 3H)

(Step 2) (3RS,4RS)-4-allyl-7-methoxymethoxy-3-(4-methoxymethoxyphenyl)-3-methylchromane

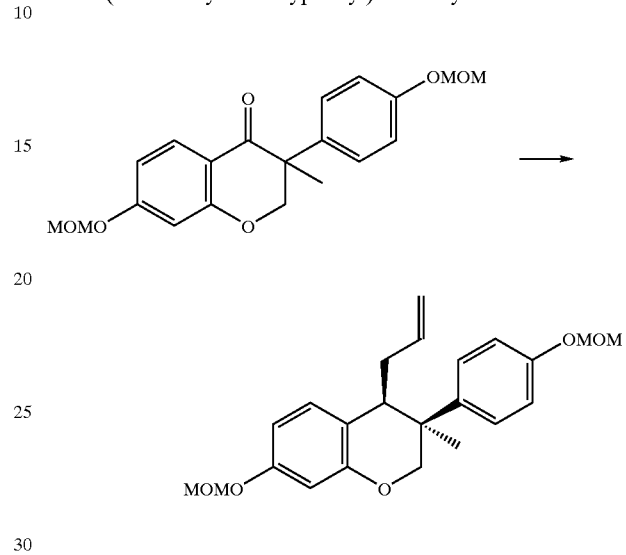

The title compound was prepared according to the same procedure as Step 6 of Example 1.

¹H-NMR(300 MHz, CDCl₃): δ7.14 (d, 2H, J=8.5 Hz), 7.03 (d, 2H, J=8.5 Hz), 6.96 (d, 1H, J=8.2 Hz), 6.59-6.54 (m, 2H), 5.68-5.54 (m, 1H), 5.17 (s, 2H), 5.14 (s, 2H), 4.86 (d, 1H, J=10.2 Hz), 4.70 (d, 1H, J=17.0 Hz), 4.52 (d, 1H, J=10.2 Hz), 4.26 (dd, 1H, J₁=2.0 and J₂=10.6 Hz), 3.48 (s, 3H), 2.81-2.79 (m, 1H), 1.37-1.19 (m, 5H)

(Step 3) (3'RS,4'RS)-ethyl 11-[7-methoxymethoxy-3-(4-methoxymethoxyphenyl)-3-methylchroman-4-yl]-2-(7,7,8,8,8-pentafluorooctyl)-9-undecenoate

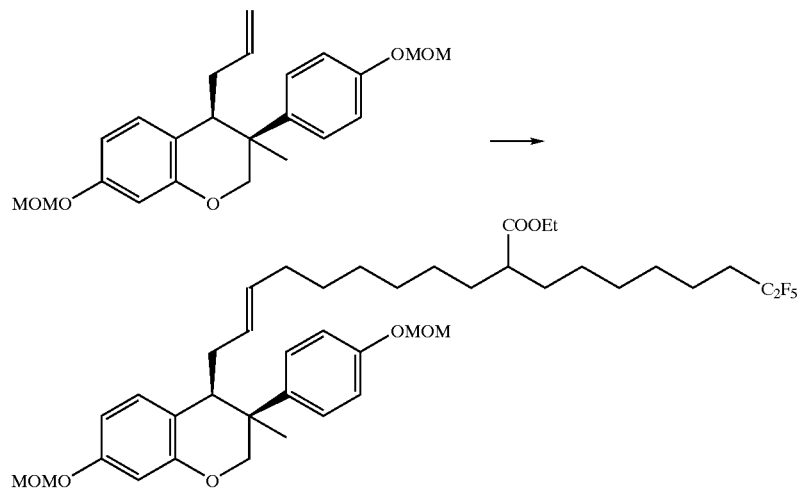

(3RS,4RS)-4-allyl-7-methoxymethoxy-3-(4-methoxymethoxyphenyl)-3-methylchromane(274 mg, 0.7 mmol), ethyl 2-(7,7,8,8,8-pentafluorooctyl)dec-9-enoate (570 mg, 1.4 mmol), and benzylidene-bis(tricyclohexylphosphine)dichlororuthenium catalyst were dissolved in dichloromethane(10 ml) and then refluxed for 12 hours. Thereafter, the reaction mixture was cooled to room temperature and concentrated under reduced pressure. The concentrate was purified by column chromatography (eluent:n-hexane/ethyl acetate=30/1, v/v) to give the title compound(330 mg, Yield 62%) as an oil.

(Step 4) (3'RS,4'RS)-ethyl 11-[7-methoxymethoxy-3-(4-methoxymethoxyphenyl)-3-methylchroman-4-yl]-2-(7,7,8,8,8-pentafluorooctyl)undecanoate was dissolved in tetrahydrofuran(10 ml), 10% Pd/C(66 mg, 20 wt %) was added thereto, and the resulting mixture was stirred for 18 hours at room temperature under hydrogen atmosphere and then filtered. The filtrate was concentrated under reduced pressure and the concentrated filtrate was purified by column chromatography (eluent:n-hexane/ethyl acetate=10/1, v/v) to give the title compound(300 mg, Yield 90%) as an oil.

$^1$H-NMR (300 MHz, CDCl$_3$): δ7.12(d, 2H, J=8.67 Hz), 7.0(d, 2H, J=8.6 Hz), 6.92(m, 1H), 6.5(m, 2H), 5.14(s, 2H), 5.10(s, 2H), 4.5(d, 1H, J=12.06 Hz), 4.23(d, 1H, J=12.06 Hz), 4.1(q, 2H), 3.49(s, 6H), 2.63(brs, 1H), 1.97-1.77(m, 6H), 1.55(m, 2H), 1.4-0.9(m, 26H)

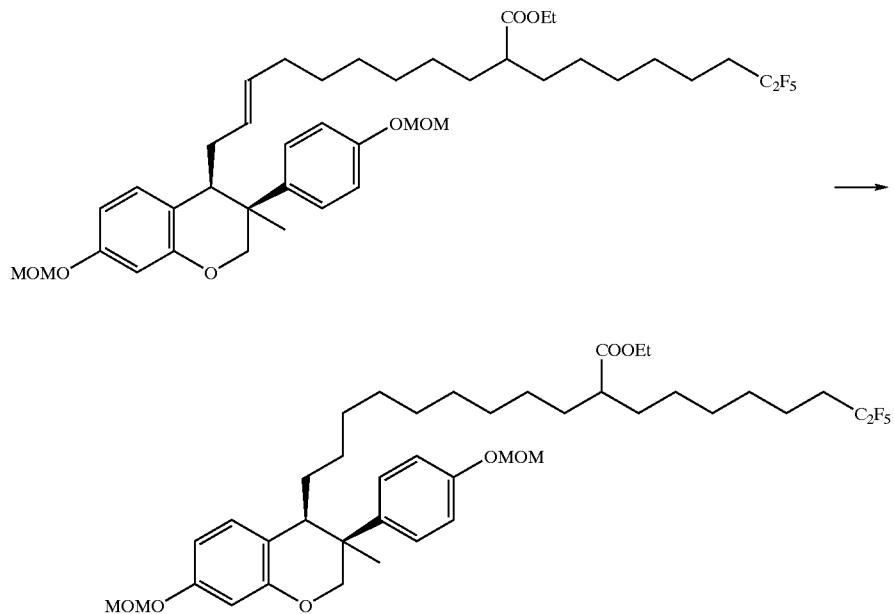

(3'RS,4'RS)-ethyl 11-[7-methoxymethoxy-3-(4-methoxymethoxyphenyl)-3-methylchroman-4-yl]-2-(7,7,8,8,8-pentafluorooctyl)-9-undecenoate(330 mg, 0.44 mmol)

(Step 5) (3'RS,4'RS)-ethyl 11-[7-hydroxy-3-(4-hydroxyphenyl)-3-methylchroman-4-yl]-2-(7,7,8,8,8-pentafluorooctyl)undecanoate

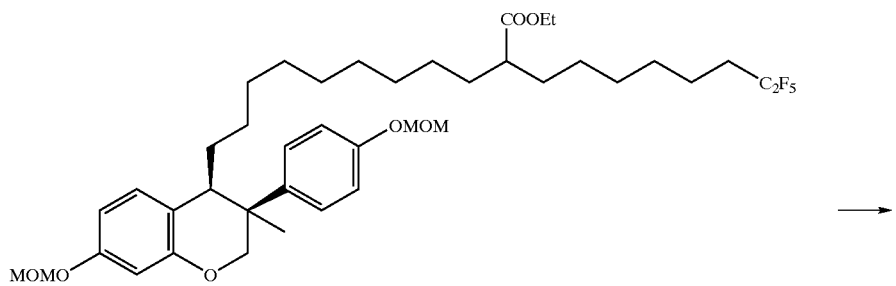

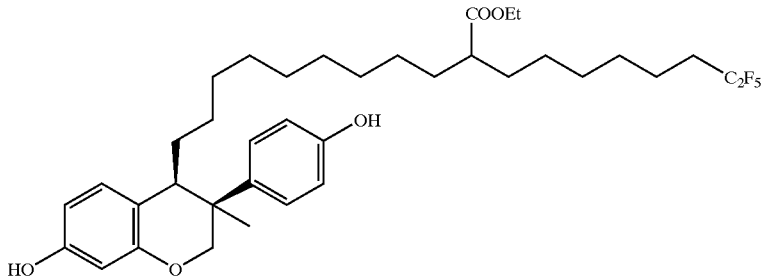

(3'RS,4'RS)-ethyl 11-[7-methoxymethoxy-3-(4-methoxymethoxyphenyl)-3-methyl-chroman-4-yl]-2-(7,7,8,8,8-pentafluorooctyl)undecanoate(300 mg, 0.39 mmol) was dissolved in methanol(10 ml), conc. hydrochloric acid(3 drops) was slowly added dropwise thereto, and the resulting mixture was stirred for 3 hours at 60° C. After the reaction was completed, the reaction mixture was cooled to room temperature, extracted with ethyl acetate, and dried over anhydrous magnesium sulfate. The solution was concentrated under reduced pressure and the residue was purified by column chromatography(eluent:n-hexane/ethyl acetate=15/1, v/v) to give the title compound(290 mg, Yield 100%) as a foam.

$^1$H-NMR (300 MHz, CDCl$_3$): δ7.13(d, 2H, J=8.6 Hz), 7.03(d, 2H, J=8.6 Hz), 6.94(m, 1H), 6.6(m, 2H), 4.53(d, 1H, J=12 Hz), 4.24(d, 1H, J=12 Hz), 4.1 (q, 2H), 2.6(brs, 1H), 1.85(m, 6H), 1.55(m, 2H), 1.4-0.9(m, 26H)

(Step 6) (3'RS,4'RS)-11-[7-hydroxy-3-(4-hydroxyphenyl)-3-methylchroman-4-yl]-2-(7,7,8,8,8-pentafluorooctyl)undecanoic acid (3'RS,4'RS)-ethyl 11-[7-hydroxy-3-(4-hydroxyphenyl)-3-methylchroman-4-yl]-2-(7,7,8,8,8-pentafluorooctyl)undecanoate(290 mg, 0.43 mmol) and potassium hydroxide (485 mg, 8.6 mmol) were dissolved in a solvent mixture of ethanol/water(10 ml/5 ml) and the resulting mixture was stirred for 12 hours at 60° C. After the reaction was completed, the reaction mixture was cooled to room temperature, acidified, by conc. hydrochloric acid, extracted with ethyl acetate, and dried over anhydrous magnesium sulfate. This solution was concentrated under reduced pressure and the residue was purified by reversed phase column chromatography(eluent:methanol/water=4/1, v/v) to give the title compound (168 mg, Yield 60%) as a foam.

$^1$H-NMR (300 MHz, CDCl$_3$): δ7.14(d, 2H, J=8.67 Hz), 7.02(d, 2H, J=8.62 Hz), 6.9(m, 1H), 6.6(m, 2H), 4.5(d, 1H, J=12.06 Hz), 4.3(d, J=12.06 Hz), 2.6 (brs, 1H), 1.85(m, 6H), 1.55(m, 2H), 1.4-0.9(m, 23H)

MS(ESI): 643(M+1)

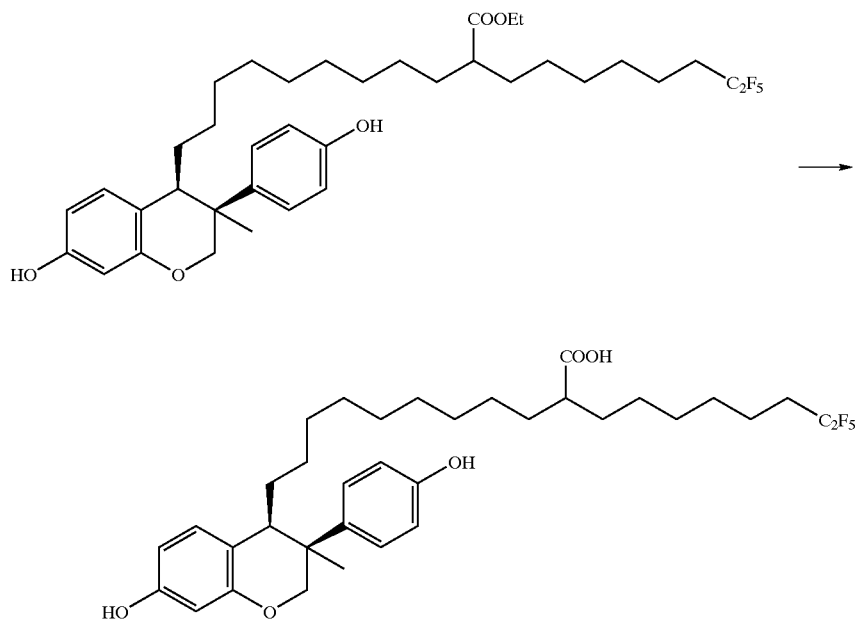

EXAMPLE 4

Synthesis of (3'RS,4'RS)-10-[7-hydroxy-3-(4-hydroxyphenyl)-3-methylchroman-4-yl]-2-(7,7,8,8,8-pentafluorooctyl)decanoic acid (Step 1) (3'RS,4'RS)-methyl 10-[7-methoxymethoxy-3-(4-methoxymethoxyphenyl)-3-methylchroman-4-yl]-2-(7,7,8,8,8-pentafluorooctyl)-8-decenoate

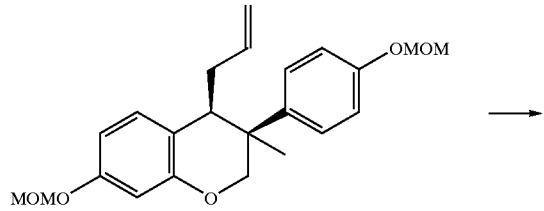

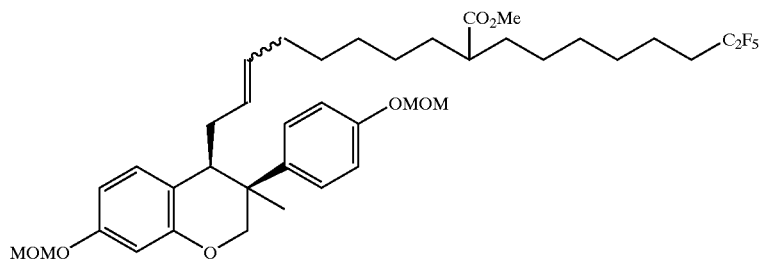

(Step 2) (3'RS,4'RS)-methyl 10-[7-methoxymethoxy-3-(4-methoxymethoxyphenyl)-3-methylchroman-4-yl]-2-(7,7,8,8,8-pentafluorooctyl)decanoate The title compound was prepared according to the same procedure as Step 3 of Example 3.

$^{1}$H-NMR (300 MHz, CDCl$_3$): δ7.20-6.88(m, 5H), 6.55 (bs, 2H), 5.40-4.90(m, 6H), 4.60-3.46(m, 1H), 4.36-4.20(m, 1H), 3.66(s, 3H), 3.50(s, 6 H), 2.72(bs, 1H), 2.40-2.20(m, 1H), 2.10-1.05(m, 27H)

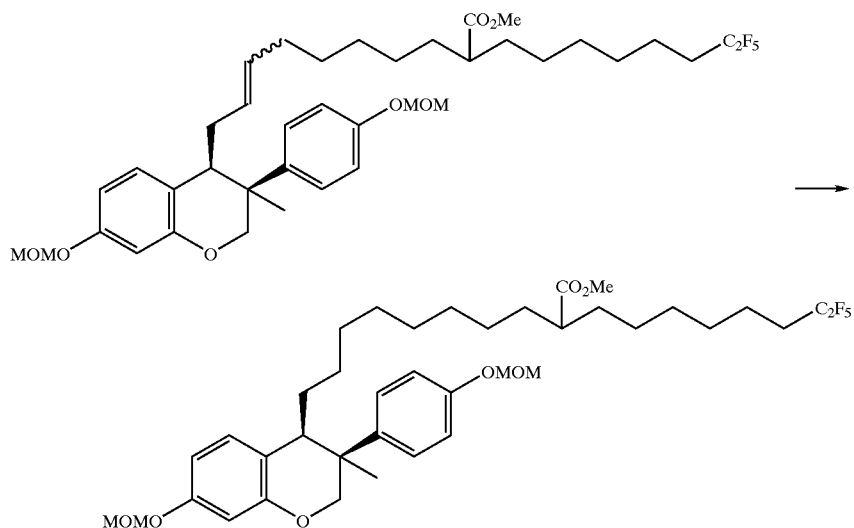

The title compound was prepared according to the same procedure as Step 4 of Example 3.

¹H-NMR (300 MHz, CDCl₃): δ7.10(d, 2H), 7.01(d, 2H), 6.98-6.90(m, 1H), 6.60-6.50(m, 2H), 5.15(s, 2H), 5.13(s, 2H), 4.50(d, 1H), 4.23(d, 1H), 3.63(s, 3H), 3.46(s, 6H), 2.62(d, 1H), 2.34-2.22(m, 1H), 2.10-1.90(m, 2H), 1.70-0.90 (m, 29H)

(Step 3) (3'RS,4'RS)-methyl 10-[7-hydroxy-3-(4-hydroxyphenyl)-3-methylchroman-4-yl]-2-(7,7,8,8,8-pentafluorooctyl)decanoate The title compound was prepared according to the same procedure as Step 6 of Example 3.

¹H-NMR (300 MHz, CDCl₃): δ7.08(d, J=8.7 Hz, 2H), 6.90(d, J=9.2 Hz, 1H), 6.83(d, J=8.6 Hz, 2H), 6.39-6.36(m, 2H), 4.50(d, J=10.4 Hz, 1H), 4.24(d, J=10.4 Hz, 1H), 2.58(bs, 1H), 2.40-2.34(m, 1H), 2.06-1.94(m, 2H), 1.70-0.95(m, 29H)

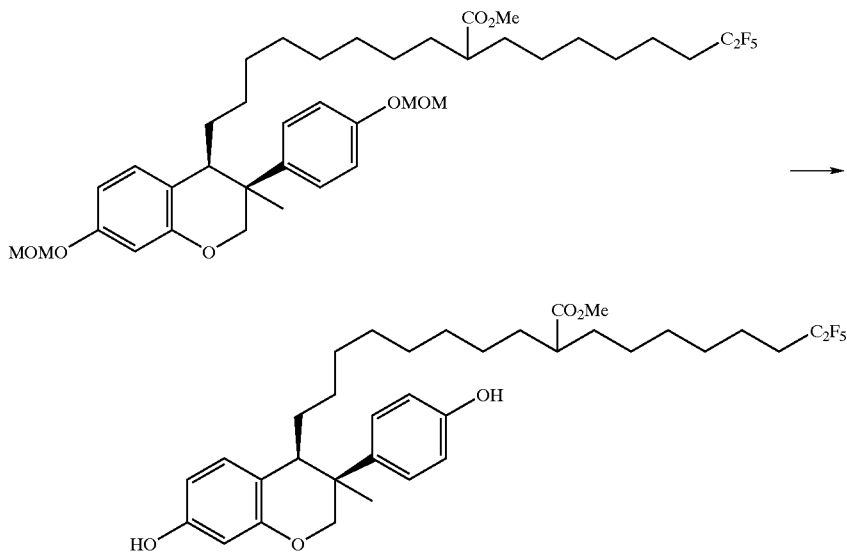

The title compound was prepared according to the same procedure as Step 5 of Example 3.

¹H-NMR (300MHz, CDCl₃): δ7.05(d, 2H), 6.85(m, 3H), 6.34(d, 2H), 6.00(bs, 1H), 4.92(d, 1H), 4.50(d, 1H), 4.15(d, 1H), 3.70(s, 3H), 2.60(bs, 1H), 2.10-1.90(m, 2H), 1.90-0.90 (m, 27H)

(Step 4) (3'RS,4'RS)-10-[7-hydroxy-3-(4-hydroxyphenyl)-3-methylchroman-4-yl]-2-(7,7,8,8,8-pentafluorooctyl)decanoic acid Industrial Applicability Experiment 1

Anti-estrogenic activity via oral administration

Oral anti-estrogenic activity in vivo of the test compound was determined according to the method described hereinafter. In this experiment, the compounds according to Examples 1, 2, 3 and 4 were used as the test compounds, and the known anti-estrogenic compound ZM189154(see: EP0124369 B1) was used as the control compound.

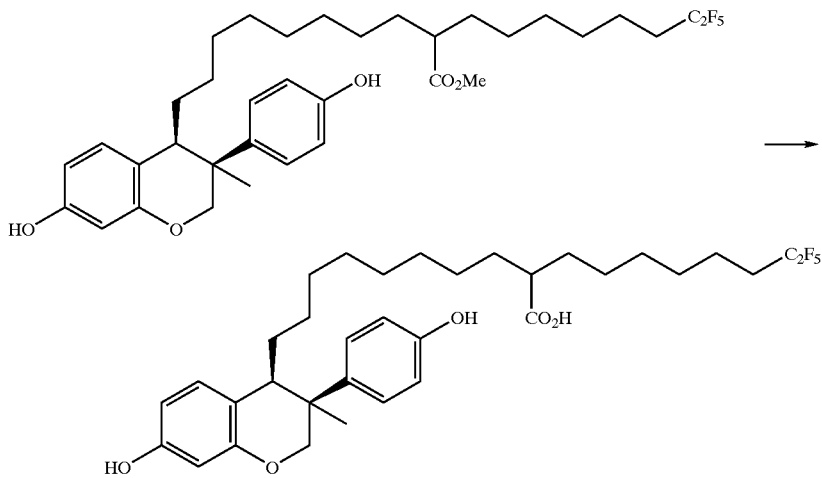

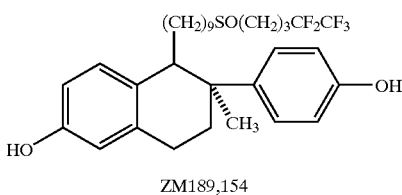

ZM189,154

Anti-estrogenic activity was determined by subcutaneously administering 17β-estradiol-benzoate(Sigma) to mice (ICR, weight 30±2 g), which were ovariectomized 2 weeks before, in the amount of 0.1 μg/day, per mouse for 3 days and then measuring the degree that the test compound inhibits the increase in uterus weight by stimulus with estradiol. In this experiment, the test compounds and the control compound were suspended in 5% arabic gum solution and orally administered for 3 days, once a day. After 24 hours from the last administration, the test animal was sacrificed and uterus was removed and weighed. The results as measured are described in the following Table 1.

TABLE 1

Anti-estrogenic activity (oral administration, 3 days)

| Test compound/dosage (p.o., 3 days) | | Inhibition (%) |
| --- | --- | --- |
| Compound of Example 1 | 10 mg/kg | 78.9 |
| Compound of Example 2 | 10 mg/kg | 62.0 |
| Compound of Example 3 | 10 mg/kg | 85.1 |
| Compound of Example 4 | 10 mg/kg | 71.4 |
| ZM189154 | 10 mg/kg | 41.7 |

From the results described in the above Table 1, it could be seen that the compound according to the present invention shows a superior inhibition activity against the increase of uterine weight by estradiol to the known anti-estrogenic control compound when administered per oral.

What is claimed is:

1. A compound of formula (1):

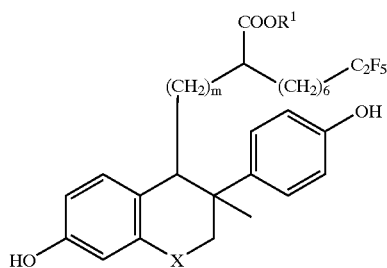

(1)

in which

X represents O or S, $R^1$ represents hydrogen or metal, and m represents an integer of 2 to 14, pharmaceutically acceptable salts, stereoisomers or hydrates thereof.

2. The compound of claim 1 wherein m is an integer of 6 to 10.

3. The compound of claim 2 wherein m is an integer of 8 or 9.

4. The compound of claim 1 wherein $R^1$ is hydrogen, alkali metal, or alkaline earth metal.

5. The compound of claim 4 wherein $R^1$ is hydrogen.

6. The compound of claim 1 wherein the stereochemical configuration of 3- and 4-position chiral carbons in the chromane(or thiochromane) ring is (3R, 4R) or (3S, 4S) or mixtures thereof.

7. The compound of claim 1 wherein the chiral carbon in the 4-position side chain of chromane (or thiochromane) ring, to which $R^1$OOC— group is attached, has the stereochemical configuration of R or S or mixtures thereof.

8. The compound of claim 1 which is selected from the group consisting of:

(3'RS,4'RS)-10-[7-hydroxy-3-(4-hydroxyphenyl)-3-methylthiochroman-4-yl]-2-(7,7,8,8,8-pentafluorooctyl)decanoic acid;

(3'RS,4'RS)-11-[7-hydroxy-3-(4-hydroxyphenyl)-3-methylthiochroman-4-yl]-2-(7,7,8,8,8-pentafluorooctyl)undecanoic acid;

(3'RS,4'RS)-11-[7-hydroxy-3-(4-hydroxyphenyl)-3-methylchroman-4-yl]-2-(7,7,8,8,8-pentafluorooctyl)undecanoic acid; and (3'RS,4'RS)-10-[7-hydroxy-3-(4-hydroxyphenyl)-3-methylchroman-4-yl]-2-(7,7,8,8,8-pentafluorooctyl)decanoic acid.

9. An anti-estrogenic pharmaceutical composition which comprises effective amount of the compound of formula (1) as defined in claim 1 as an active component together with pharmaceutically acceptable carriers.

10. The anti-estrogenic pharmaceutical composition of claim 9, which is used for the treatment of breast cancer.

11. The anti-estrogenic pharmaceutical composition of claim 10, which is formulated to an oral preparation.

* * * * *